(12) United States Patent
Iwai et al.

(10) Patent No.: US 10,517,993 B2
(45) Date of Patent: Dec. 31, 2019

(54) POROUS COMPOSITE, BONE REGENERATION MATERIAL, AND METHOD FOR PRODUCING POROUS COMPOSITE

(71) Applicant: TOYOBO CO., LTD., Osaka-shi, Osaka (JP)

(72) Inventors: Atsushi Iwai, Otsu (JP); Fumihiko Kajii, Otsu (JP); Hidenori Tanaka, Otsu (JP)

(73) Assignee: TOYOBO CO., LTD., Osaka (JP)

( * ) Notice: Subject to any disclaimer, the term of this patent is extended or adjusted under 35 U.S.C. 154(b) by 0 days.

(21) Appl. No.: 15/529,004

(22) PCT Filed: Jun. 12, 2015

(86) PCT No.: PCT/JP2015/067061
§ 371 (c)(1),
(2) Date: May 23, 2017

(87) PCT Pub. No.: WO2016/084413
PCT Pub. Date: Jun. 2, 2016

(65) Prior Publication Data
US 2017/0304492 A1    Oct. 26, 2017

(30) Foreign Application Priority Data

Nov. 27, 2014  (JP) ................................ 2014-239509
Jan. 28, 2015  (WO) .................. PCT/JP2015/052327

(51) Int. Cl.
| | | |
|---|---|---|
| *A61L 27/24* | (2006.01) | |
| *A61K 33/42* | (2006.01) | |
| *A61L 27/12* | (2006.01) | |
| *A61L 27/54* | (2006.01) | |
| *A61L 27/56* | (2006.01) | |

(52) U.S. Cl.
CPC .............. *A61L 27/24* (2013.01); *A61K 33/42* (2013.01); *A61L 27/12* (2013.01); *A61L 27/54* (2013.01); *A61L 27/56* (2013.01); *A61L 2430/02* (2013.01)

(58) Field of Classification Search
CPC ...... A61L 2430/02; A61L 27/24; A61L 27/56; A61L 27/12; A61L 27/54; A61L 27/425; A61K 33/42
See application file for complete search history.

(56) References Cited

U.S. PATENT DOCUMENTS

| | | | | | |
|---|---|---|---|---|---|
| 4,970,298 | A * | 11/1990 | Silver | ...................... | A61K 9/70 128/DIG. 8 |
| 9,034,356 | B2 * | 5/2015 | Shimp | .................... | A61L 27/446 424/423 |
| 9,119,903 | B2 * | 9/2015 | Tanaka | .................... | A61L 27/50 |
| 9,168,327 | B2 * | 10/2015 | Wang | .................. | A61L 27/3608 |
| 2002/0042657 | A1 * | 4/2002 | Pugh | ....................... | A61K 35/32 623/23.56 |
| 2004/0028738 | A1 * | 2/2004 | Huang | ..................... | A61K 9/70 424/484 |
| 2005/0042252 | A1 | 2/2005 | Tanaka et al. | | |
| 2006/0135921 | A1 * | 6/2006 | Wiercinski | ........... | A61K 8/0208 604/368 |
| 2006/0199876 | A1 * | 9/2006 | Troczynski | ............. | A61L 27/32 523/115 |
| 2007/0128245 | A1 * | 6/2007 | Rosenberg | ........... | A61K 9/0024 424/423 |
| 2007/0134285 | A1 * | 6/2007 | Lynn | ................... | A61L 24/0084 424/423 |
| 2008/0234396 | A1 | 9/2008 | Shoji et al. | | |
| 2009/0012625 | A1 | 1/2009 | Ying et al. | | |
| 2009/0149634 | A1 | 6/2009 | Shoji et al. | | |
| 2009/0166580 | A1 | 7/2009 | Tanaka et al. | | |
| 2009/0210057 | A1 * | 8/2009 | Liao | ................... | A61F 2/30756 623/14.12 |
| 2011/0033552 | A1 | 2/2011 | Shoji | | |
| 2013/0177648 | A1 * | 7/2013 | O'Brien | .................. | A61L 27/46 424/484 |

FOREIGN PATENT DOCUMENTS

| | | |
|---|---|---|
| CN | 101048182 A | 10/2007 |
| CN | 101084025 A | 12/2007 |
| CN | 102014974 A | 4/2011 |
| EP | 1615676 A2 | 1/2006 |
| EP | 1964583 A1 | 9/2008 |

(Continued)

OTHER PUBLICATIONS

Matsuno et al. Development of β-tricalcium Phosphate/Collagen Sponge Composite for Bone Regeneration. Dental Materials Journal 25 ( 1 ) : 138-144, 2006. (Year: 2006).*

(Continued)

*Primary Examiner* — Robert A Wax
*Assistant Examiner* — Olga V. Tcherkasskaya
(74) *Attorney, Agent, or Firm* — Westerman, Hattori, Daniels & Adrian, LLP

(57) ABSTRACT

Provided are a porous composite containing OCP and collagen having higher compressive strength than before; a bone regeneration material containing the same; and a method for producing a porous composite. The porous composite contains octacalcium phosphate and collagen, has a pore size of 5 μm to 40 μm as determined by measurement using a mercury porosimeter, and contains pores of 71 μm to 200 μm at a rate of less than or equal to 8% in all pores of less than or equal to 200 μm.

17 Claims, 5 Drawing Sheets

(56) References Cited

FOREIGN PATENT DOCUMENTS

| | | | |
|---|---|---|---|
| EP | 2231210 A1 | 9/2010 | |
| JP | 5-70113 A | 3/1993 | |
| JP | 6-304242 A | 11/1994 | |
| JP | 2003-260124 A | 9/2003 | |
| JP | 2005-279078 A | 10/2005 | |
| JP | 2006-167445 A | 6/2006 | |
| JP | 2007-98118 A | 4/2007 | |
| JP | 2008-295791 A | 12/2008 | |
| JP | 2009-132601 A | 6/2009 | |
| JP | 2009-254547 A | 11/2009 | |
| JP | 2010-273847 A | 12/2010 | |
| WO | 2005/004928 A2 | 1/2005 | |
| WO | 2006/031196 A1 | 3/2006 | |
| WO | 2009/076594 A1 | 6/2009 | |

OTHER PUBLICATIONS

Zhang et al. The development of collagen based composite scaffolds for bone regeneration. Bioactive Materials 3 (2018) 129-138. (Year: 2018).*

Kawai et al. First Clinical Application of Octacalcium Phosphate Collagen Composite in Human Bone Defect. Tissue Engineering: Part A, 2014, 20(7-8):1336-1341. (Year: 2014).*

Tanuma et al., "Granule Size-Dependent Bone Regenerative Capacity of Octacalcium Phosphate in Collagen Matrix", Tissue Engineering: Part A, Mar. 2012, vol. 18, Nos. 5 and 6, pp. 546-557, cited in ISR and Japanese Decision to Grant a Patent (15 pages).

Kawai et al., "First Clinical Application of Octacalcium Phosphate Collagen Composite in Human Bone Defect", Tissue Engineering: Part A, Apr. 1, 2014, vol. 20, Nos. 7 and 8, pp. 1336-1341, cited in Japanese Decision to Grant a Patent (6 pages).

Decision to Grant a Patent dated Mar. 22, 2016, issued in counterpart Japanese Patent Application No. 2015-547178, w/English translation (4 pages).

International Search Report dated Sep. 1, 2015, issued in counterpart International Application No. PCT/JP2015/067061 (2 pages).

Legeros, Racquel Z., "Preparation of Octacalcium Phosphate (OCP): A Direct Fast Method", Calcified Tissue International, 1985, vol. 37, pp. 194-197.

Extended (Supplementary) European Search Report dated Jun. 20, 2018, issued in counterpart application No. 15862805.7. (8 pages).

Office Action dated Jun. 24, 2019, issued in counterpart CN application No. 201580063040.3, with English translation. (18 pages).

Tanuma Yuji el at., "Granule Size-Dependent Bone Regenerative Capacity of Octacalcium Phosphate in Collagen Matrix", Tissue Engineering, Part A, 2012, vol. 18, No. 5 and 6, pp. 546-557, cited in CN Office Action dated Jun. 24, 2019. (12 pages).

Zhao Kang el at., "Fabrication of Hydroxyapatite Porous Scaffolds by Freeze Drying", Journal of the Chinese Ceramic Society, Mar. 2009, vol. 37, No. 3, pp. 432-435, with English abstract, cited in CN Office Action dated Jun. 24, 2019. (6 pages).

\* cited by examiner

POROUS COMPOSITE, BONE REGENERATION MATERIAL, AND METHOD FOR PRODUCING POROUS COMPOSITE

TECHNICAL FIELD

The present invention relates to a porous composite, a bone regeneration material, and a method for producing a porous composite.

BACKGROUND ART

As conventionally used bone regeneration materials, calcium phosphates such as hydroxyapatite (HA) are known (see, for example, JP2010-273847, JP2003-260124, JP2009-132601, and JP2005-279078).

Recently, octacalcium phosphate (hereinafter, referred to as "OCP") which is a precursor of HA has been proved to have higher action of promoting bone regeneration and higher bioabsorbability than other calcium phosphates such as HA and β-tricalcium phosphate (β-TCP) do (see, for example, JP2006-167445). Thus, OCP has especially excellent characteristics as a bone regeneration material among other calcium phosphates.

However, OCP is poor in shape-imparting property because it is an inorganic substance. Therefore, it is difficult to apply OCP by itself to regenerate an extensive bone defective part or the like. In light of this difficulty, use of a composite of OCP and collagen as a bone regeneration material has been proposed (see, for example, JP2006-167445).

SUMMARY OF INVENTION

Technical Problems

Bone regeneration materials are generally applied to indefinite bone defects. Bone regeneration materials are required to have excellent handling property in application into a body or the like in addition to the capability of promoting bone regeneration. However, a composite of OCP and collagen for use as a bone regeneration material is required to be a porous body to function as a scaffold of osteoblasts for bone regeneration. Such a porous composite generally has low compressive strength, and is easily damaged during handling, and thus has a problem of poor operability.

The present invention has been devised in light of the aforementioned problems, and it is an object of the present invention to provide a porous composite containing OCP and collagen having higher compressive strength than before, a bone regeneration material containing the same, and a method for producing a porous composite.

Solutions to Problems

A bone regeneration material formed of a porous composite and having a porous structure realizes internal bone formation of allowing osteoblasts to enter inside the porous structure and promoting formation of new bone. For allowing entry of osteoblasts, a certain pore size is required. Generally, a larger pore size makes entry of osteoblasts inside the porous structure easier. Meanwhile, the present inventors found that the strength of the porous composite is weakened as the pore size increases. The inventors made diligent efforts and found a porous composite that effectively functions as a scaffold for bone regeneration by allowing easy entry of osteoblasts inside the same owing to a specific pore size, and that has moderate strength, good handleability during a clinical operation or the like, and excellent operability. The present invention provides the invention represented by the following aspects.

(1) A porous composite containing octacalcium phosphate and collagen, having a pore size of 5 μm to 40 μm as determined by measurement using a mercury porosimeter, and containing pores of 71 μm to 200 μm at a rate of less than or equal to 8% in all pores of less than or equal to 200 μm.

(2) A bone regeneration material containing the porous composite according to (1).

(3) A method for producing a porous composite containing octacalcium phosphate and collagen, the method including the step of:

clipping and freezing a gel, sol or liquid containing octacalcium phosphate and collagen in a liquid refrigerant.

(4) A porous composite containing octacalcium phosphate and collagen obtained by the method according to (3).

Advantageous Effects of Invention

According to the present invention, it is possible to provide a porous composite containing OCP and collagen that is higher in compressive strength than before, a bone regeneration material containing the same, and a method for producing a porous composite. The porous composite of the present invention allows entry of osteoblasts inside the same and promotes bone regeneration owing to a specific pore size. Owing to moderate compressive strength, the porous composite has such excellent effects that it can be easily worked, e.g., cut in accordance with the shape of the bone defective part with forceps or the like in an operation or the like, and it is less likely to be damaged in handling.

DESCRIPTION OF EMBODIMENTS

[Porous Composite]

Figure 1:
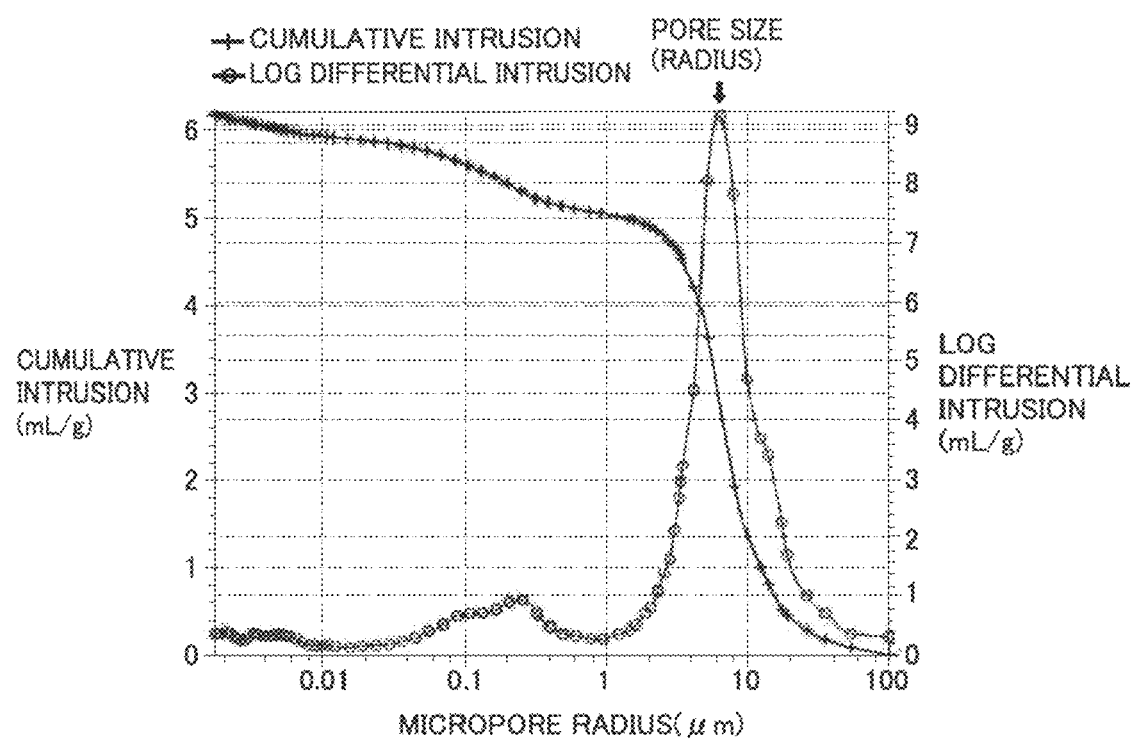
FIG. 1 is a graph showing a micropore distribution curve in measurement of pore size in Example 1.

The porous composite of the present invention is a porous composite containing octacalcium phosphate and collagen OCP/collagen composite). A preferred embodiment of the porous composite of the present invention is a porous composite in which collagen is randomly present three-dimensionally in a fibrous or film form and forms a spongy structure, and OCP is present as granules in the spongy structure.

OCP ($Ca_8H_2(PO_4)_6 \cdot 5H_2O$) can be prepared by various known methods. For example, OCP can be prepared, for example, by a LeGeros dropping test (LeGeros R Z, Calcif Tissue Int 37: 194-197, 1985) or by a method in which a synthesizer (triple flow tube) is used as disclosed in JP5-

070113. OCP can also be prepared by a mixing method. Concretely, OCP can be obtained, for example, by mixing an aqueous solution of sodium dihydrogen phosphate with an aqueous solution of calcium acetate under an appropriate condition and collecting the produced precipitate. Preferably, OCP obtained from the precipitate is dried and ground by using an electric mill or the like, and used in the form of a particulate powder. The particle size of the prepared powder preferably ranges from 10 μm to 1000 μm, and more preferably ranges from 300 μm to 500 μm.

As collagen, various collagens can be used while the origin, properties and the like thereof are not particularly limited. Preferably an enzymatically solubilized collagen is used, which is obtained by solubilizing collagen with a protease (e.g., pepsin or pronase) and from which telopeptide has been removed. As the type of collagen, type I, type II, type III and type IV collagens which are fibrous collagens are preferred, and type I collagen that is abundantly contained in a living body, or a mixture of type I and type III collagens is particularly preferred. While the raw material of collagen is not particularly limited, collagen derived from skin, bone, tendon or the like of swine, bovine or the like can be preferably used. Collagen, which is a biological component, advantageously has high safety, and in particular, enzymatically solubilized collagen is preferred because of its low allergenicity. As the collagen, a commercially available product may be used.

In the porous composite of the present invention, a mixing ratio between OCP and collagen can be appropriately adjusted depending on the desired shape-imparting property, operability, biocompatibility and the like. The mixing ratio of OCP to 1 part by weight of collagen is preferably 0.5 parts by weight to 35 parts by weight, more preferably 1 part by weight to 20 parts by weight, further preferably 2 parts by weight to 10 parts by weight. This is because if the ratio of OCP is less than 0.5 to the ratio of collagen of 1, the bone regenerating function of the obtained composite would be poor, and if it is more than 35, the shape-imparting property would be deteriorated.

Preferably, the porous composite of the present invention has a pore size of 5 μm to 40 μm. If the pore size exceeds 40 μm, the compressive strength of the porous composite tends to reduce to less than 0.3 MPa. On the other hand, if the pore size is less than 5 μm, cells of the bone metabolic system such as osteoblasts are difficult to enter the porous composite, and the action of promoting bone regeneration would be deteriorated.

The porous composite of the present invention more preferably has a pore size of 7 μm to 36 μm, further preferably 10 μm to 20 μm.

Pore size is measured by using a micropore distribution measurement using a mercury porosimeter, and concretely, it is measured by the following method.

(Measurement of Pore Size)

As a pretreatment, samples are dried at a constant temperature of 120° C. for 4 hours. For each of the samples after the pretreatment, the micropore distribution for a micropore size of 0.0018 μm to 200 μm is determined under the following conditions by a mercury intrusion method using the following measurement device.

Measurement device: AutoPore IV9520 (Available from Micromeritics Japan)

Measuring Conditions:

Contact angle between sample and mercury: 140 deg

Surface tension of mercury: 0.48 N/m (converted by 1 dyne=$10^{-5}$ N)

The pore size in the present invention refers to the value of micropore size showing the maximum value of the peak having the largest area in the micropore distribution curve obtained from the measuring pressure by the mercury intrusion method.

Further, the porous composite of the present invention is characterized by containing pores of 71 μm to 200 μm at a rate of less than or equal to 8% in all pores of less than or equal to 200 μm, in the aforementioned micropore distribution determined by the mercury intrusion method. Preferably, the rate is 3% to 8%.

The rate of pores is represented by the following formula using a cumulative micropore volume and a total micropore volume measured by the mercury porosimeter.

Rate of pores (%)=cumulative micropore volume/total micropore volume)×100

This means that the porous composite of the present invention has a relatively narrow distribution of pores, and has more uniform pore sizes. This makes it possible to provide a uniform cell scaffold over the entire porous composite, and give uniform structural characteristics. Conventionally, it is difficult to realize more uniform micropores. For example, TANUMA Y et al. (TISSUE ENGINEERING: Part A, Volume 18, Numbers 5 and 6, 2012) disclose a composite containing OCP and collagen, having a pore size of less than or equal to 30 μm. However, as a result of analysis of the micropore distribution curve disclosed in TANUMA Y. et al. made by the present inventors, the rate of pores of greater than or equal to 71 μm in all pores was about 9% to 15%. Thus, the micropore distribution is broad, and a relatively large quantity of pores have large pore sizes.

Owing to the pore size in the aforementioned range, the porous composite of the present invention is high in compressive strength. The compressive strength of the porous composite is preferably greater than or equal to 0.3 MPa, more preferably greater than or equal to 0.3 MPa and less than or equal to 3.0 MPa, further preferably greater than or equal to 0.3 MPa and less than or equal to 1.0 MPa. If the compressive strength is less than 0.3 MPa, the operability of the porous composite tends to deteriorate. To be more specific, if the porous composite of the present invention collapses, or pores are crushed when a bone defective part is filled with the porous composite, an adverse effect is exerted on the subsequent bone regeneration. Concretely, when a physician conducts an operation of filling a bone defective part having a diverse shape with the porous composite without leaving any clearance with the use of a jig, the index indicating that collapse of the composite or crush of pores does not occur is a compressive strength of greater than or equal to 0.3 MPa. Although the upper limit of the compressive strength is not particularly specified, it is preferably lower than or equal to 3.0 MPa from the view point of ease of operation in filling a bone defective part.

Compressive strength in the present invention is measured by the following method.

(Measurement of Compressive Strength)

In an environment at a temperature of 25° C. and a humidity of 65%, a cylindrical specimen (sample) having a diameter of 9.0 mm and a height of 15 mm is dipped in a phosphate buffered saline (10 mM sodium phosphate, 0.14

M sodium chloride, pH 7.4) for 30 minutes. Then, the water on the surface of the sample is lightly wiped, and a uniaxial load is applied in the vertical direction of the cylinder by using a tension and compression tester (load cell capacity: 1 kN). The load is varied stepwise, and the least load at which the sample collapses is determined as a load at collapse. The wording "collapse of the sample is observed" means that occurrence of a clear crack or peeling is confirmed when the sample is visually observed. The visual observation can be conducted by macroscopic observation, and in the case where macroscopic observation is difficult, a method of enlarging and imaging the sample with a video camera or the like, and observing the sample on the monitor by visual observation can also be used.

Figure 2:
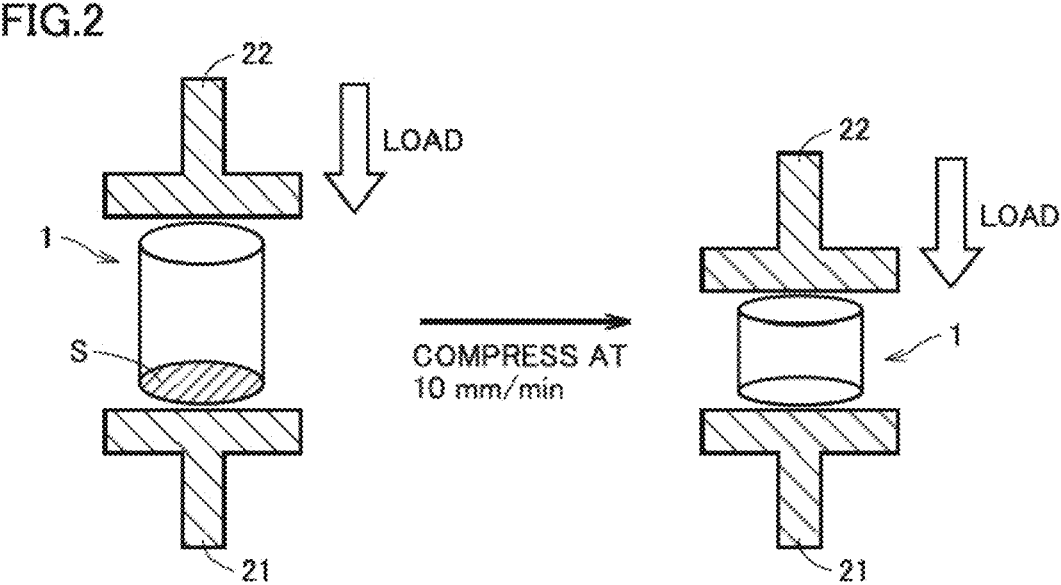
FIG. 2 is a schematic view illustrating a method for measuring compressive strength.

To be more specific, referring to FIG. 2, after setting a sample 1 on a sample stage 21, a crosshead (pressing jig) 22 is lowered at a speed of 10 mm/min, and when the load cell indicates 2.5 N, crosshead 22 is stopped to release the sample from the load. The sample on the sample stage is observed, and if is not collapsed, the sample is returned to the sample stage and set again, and the crosshead is lowered similarly until the load cell indicates 5 N. This operation is repeated while the load is increased by 2.5 N every time, and the load when collapse of the sample is first observed is determined as a load at collapse.

Compressive strength in the present invention is represented by formula 1, from the load at collapse, and the sectional area of the sample (sectional area in the section perpendicular to the thickness direction of the cylinder).

$$Cs=F/S \quad \text{(Formula 1)}$$

Cs: Compressive strength (Pa)
F: Load at collapse (N)
S: Sectional area of sample ($m^2$)

Porosity (percentage of voids) of the porous composite is preferably 80% to 98%, more preferably 85% to 95%. It is further preferably 85% to 90%. Porosity is determined by the following formula 2 from the total micropore volume measured by the mercury intrusion method and the apparent density.

$$\text{Porosity (\%)=total micropore volume}/\{(1/\text{apparent density})+\text{total micropore volume}\}\times 100 \quad \text{(Formula 2)}$$

The shape of the porous composite of the present invention is preferably a rectangular parallelepiped (block body), a cylinder or a tablet, or a granule. When the porous composite is a rectangular parallelepiped, the size is preferably greater than or equal to 5 mm×5 mm×5 mm, and generally, the upper limit is preferably in the range of less than or equal to 100 mm×100 mm×100 mm. The rectangular parallelepiped is not limited to a cube. When the porous composite is cylindrical, the diameter is preferably 5 mm to 50 mm, and the height is preferably within the range of 1 mm to 50 mm. When the porous composite is granular, the shape of the granule may be indefinite without limited to sphere, but the porous composite preferably has a diameter of 0.1 mm to 10 mm.

The porous composite of the present invention is used in such a manner that a bone defective part is supplied with the porous composite. When sufficient blood or body fluid is present in the bone defective part, the bone defective part can be supplied with the porous composite as it is, or with the porous composite cut into an appropriate shape. When sufficient blood or the like is not present in the bone defective part, or when the porous composite cannot be supplied in its original form, the porous composite is dipped in blood, saline or the like, and the bone defective part can be supplied with the porous composite after the porous composite is confirmed to exhibit spongy elasticity.

[Method for Producing Porous Composite]

As a method for producing a porous composite of the present invention, a production method of mixing OCP with collagen is preferred, and a production method as mentioned below can be used.

(a) Method of Making Composite by Mixing OCP With Collagen

First, OCP is added to a collagen solution of which concentration, pH and the like are adjusted to the ranges that allow gelation, and they are kneaded sufficiently to prepare a mixture of OCP and collagen. Then, the mixture is molded in an appropriate mold, and frozen, and lyophilized to obtain a composite. The obtained composite is subjected to a dehydrothermal cross-linking treatment, and further sterilized by a commonly used sterilization method (for example, γ-ray irradiation, electron beam irradiation, or ethylene oxide gas).

(b) Method of Making Composite by Mixing OCP Suspension

A collagen acidic solution having an appropriate concentration is aseptically adjusted in an appropriate buffer (for example, a phosphate buffer, a Tris buffer, or a sodium acetate buffer) to a pH of 5.5 to 7.5, and OCP is added to the solution before collagen gelates, to prepare a suspension of collagen and OCP. Thereafter, the suspension is poured into a mold while its pH is kept neutral or weak alkaline to impart a shape to the suspension. Then, the suspension is gelated at an appropriate temperature (for example, 37° C.), and washed repeatedly with water to remove the salt or the like in the buffer to give a composite carrier, followed by lyophilization and sterilization in the same manner as described above.

(c) Method of Making Composite by Precipitating OCP on Collagen

A collagen acidic solution having an appropriate concentration is aseptically adjusted in an appropriate buffer (for example, a phosphate buffer, a Tris buffer, or a sodium acetate buffer) to a pH of 5.5 to 7.5, and a calcium solution and a phosphoric acid solution are added to the solution before collagen gelates, to precipitate OCP on collagen. Thereafter, the solution is poured into a mold while its pH is kept neutral or weak alkaline to impart a shape to the solution. Then, gelation is allowed at an appropriate temperature (for example, 37° C.). Then salt or the like in the buffer is removed by washing repeatedly with water to give a composite carrier, followed by lyophilization and sterilization in the same manner as described above.

Precipitation of OCP is based on the degree of supersaturation (ion product/solubility product) determined by $Ca^{2+}$, $PO_4^{3-}$, pH and the like. Therefore, it is possible to precipitate OCP by pouring a $Ca^{2+}$ solution and a $PO_4^{3-}$ solution into a collagen solution having adjusted pH, under such a condition that they are supersaturated for OCP. OCP precipitates spontaneously in collagen gaps, or precipitates from the surface of collagen fibers as a nucleus.

Preferably, the method for producing a porous composite of the present invention includes, after dipping and freezing a gel, sol, or liquid containing octacalcium phosphate and collagen in a liquid refrigerant, the step of lyophilizing the resultant product. The wording "dipping and freezing a gel, sol, or liquid in a liquid refrigerant" also means such a form that, for example, after hermetically sealing a vessel containing a gel, sol or liquid, the vessel is dipped in a liquid refrigerant to freeze the gel, sol or liquid.

The liquid refrigerant is a liquid having a temperature lower than the freezing temperature of the gel, sol or liquid containing octacalcium phosphate and collagen, and examples of the liquid refrigerant include methanol, ethanol, acetone, acetonitrile, and liquid nitrogen. The temperature of the liquid refrigerant is preferably less than or equal to −20° C., more preferably less than or equal to −40° C., further preferably less than or equal to −80° C.

It is supposed that by rapidly freezing the gel, sol or liquid containing octacalcium phosphate and collagen by dipping in the liquid refrigerant, the pore size of the obtainable porous composite can be made small. Conventionally, methods of freezing in a freezer at −20° C. or in a deep freezer at −80° C. have been widely known. The capability of producing the porous composite at relatively high temperatures such as −40° C. and −80° C., as well as with liquid nitrogen at −196° C., by using the liquid refrigerant is one of the features of the present invention, and the present invention has an advantageous effect in the finding that the magnitude of pore size does not depend only on the temperature.

Preferably, the porous composite of the present invention is subjected to a heat treatment. The heat treatment collapses part of the OCP molecular structure to allow cells of the bone formation system to enter more easily, so that bone regeneration is promoted, and the shape retentivity is improved by cross-linking of collagen.

The temperature of the heat treatment is preferably 50° C. to 200° C., more preferably 60° C. to 180° C. The heat treatment is preferably conducted under a reduced pressure. The pressure is preferably 0 Pa to 3000 Pa, more preferably 0 Pa to 300 Pa. The treatment time of the heat treatment is preferably 0.1 days to 10 days, more preferably 0.5 days to 5 days.

[Bone Regeneration Material]

The present invention further relates to a bone regeneration material containing the aforementioned porous composite. The bone regeneration material can be used for repair of bone defects in the dental/oral surgery field or the orthopedic surgery field, or repair of bone defects after craniotomy or thoracotomy. For example, in the dental/oral surgery field, by supplying a bone defect generated by periodontal disease, cystic cavity, atrophy of alveolar process, cleft jaw part, tooth extraction socket or the like with the hone regeneration material formed of the porous composite, an excellent bone regenerative effect is observed after several weeks to several months. In the orthopedic surgery field, for example, for a hone defect after excision of bone tumor, or a hone defect generated by injury such as fracture, hone regeneration can be promoted by supplying the bone defective part with the present bone regeneration material.

The bone regeneration material may contain, for example, cytokine (bone morphogenetic protein-2, transforming growth factor β1, etc.) having a bone forming ability besides OCP and collagen, and such cytokine can increase the bone regeneration speed.

The bone regeneration material may contain other ingredients that are commonly used in the present field besides the above. Examples of such ingredients include bioabsorbable polymers (polyglycolic acid, polylactic acid, polylactic acid-polyethylene glycol copolymer etc.), and bioabsorbable calcium phosphates other than OCP (β-TCP etc.).

EXAMPLES

Hereinafter, the present invention will be described more specifically by way of examples, however, the present invention is not limited to these examples.

Example 1

(1) Preparation of OCP

First, Solution 1 and Solution 2 for preparing OCP were prepared in the following manner.

[Solution 1] In 2500 g of distilled water, 31.2 g of sodium dihydrogen phosphate dihydrate was dissolved to prepare Solution 1.

[Solution 2] In 2500 g of distilled water, 35.2 g of calcium acetate monohydrate was dissolved to prepare Solution 2.

Then, Solution 1 was put in a separable flask, and the temperature was elevated to 70° C. by a mantle heater. Then, a stirring blade (blade diameter: 12 cm) was attached to a stirrer (MAZELA Z available from TOKYO RIKAKIKAI CO., LTD.), and Solution 2 was added dropwise to Solution 1 at a rate of about 28 mL/min under stirring at 250 rpm. After end of the dropping, the mixture of Solution 1 and Solution 2 was further stirred at 70° C., 250 rpm for 2 hours.

Then, the precipitate produced in the mixture was filtered through a membrane filter (pore size 3 μm, A300A293C, available from Advantec Toyo Kaisha Ltd.) and collected. The collected precipitate was dispersed in 1500 mL of distilled water, and washed by stirring for 15 minutes. These filtering and washing steps were repeated three more times.

Then, the precipitate after washing was dried at 30° C. for 24 hours using a constant temperature drier. The precipitate after drying was ground by an electric mill, and the particles were classified by a sieve to have particle sizes of 300 μm to 500 μm, and thus a powder was obtained. Lastly, the obtained powder was subjected to dry heat sterilization at 120° C. for 2 hours.

(2) Preparation of OCP/Collagen Composite (Porous Composite)

In 200 parts by weight of distilled water cooled to 4° C., 1 part by weight of collagen derived from swine dermis (NMP collagen PS, available from NH Foods Ltd.) containing type I and type III collagens was dissolved, to obtain an about 0.5% by weight collagen solution. A sodium hydroxide aqueous solution was added to the collagen aqueous solution while the liquid temperature was kept at 4° C., and pH was adjusted to about 7.4 to prepare a collagen suspension. Then, to the collagen suspension, OCP (particle size: 300 μm to 500 μm) was added so that the weight ratio between collagen and OCP would be 77:23, and then the mixture was further stirred at room temperature to obtain an OCP/collagen suspension.

Then, the obtained OCP suspension was put in a centrifugal bottle, and centrifuged by a centrifugal force of 7000×g for 20 minutes by using a centrifuge (GRX-250, available from TOMY SEIKO CO., LTD.). Then, the supernatant was removed so that the amount of collagen in the OCP/collagen suspension would be 3% by weight, and then the contents were mixed for about 2 minutes with a spatula, to obtain an OCP/collagen composite gel. The gel was put in a plastic vessel (inside diameter: 8.5 mm, capacity: about 3.0 cm$^3$) having a cylindrical internal space, and centrifuged with a centrifugal force of 230×g for 1 minute to remove bubbles.

The vessel was hermetically sealed, and rapidly frozen by dipping in a large excess of methanol cooled to −80° C. relative to the capacity of the product to be frozen. After opening the vessel, the frozen product was dried by a lyophilizer (−10° C., 48 hours) and molded. Then, the molded product was heated at 150° C. for 24 hours under reduced pressure to conduct dehydrothermal cross-linking, followed by cutting into a piece of 1.5 mm or 15 mm thick with a surgical knife. Lastly, sterilization was conducted by irradiation with the electron beam (15 kGy). In this manner, the porous composite (OCP: collagen composite) in Example 1 was obtained.

Examples 2 and 3, and Comparative Examples 1 and 2

In Example 2, freezing of the product to be frozen was conducted by using liquid nitrogen at −196° C. In Example 3, freezing of the product to be frozen was conducted by using methanol cooled to −40° C. In Comparative Example 1, freezing of the product to be frozen was conducted by using a freezer set at −80° C. In Comparative Example 2, freezing of the product to be frozen was conducted by using a freezer set at −20° C.

Porous composites (OCP/collagen composites) of Examples 2 and 3, and Comparative Examples 1 and 2 were obtained in the same manner as in Example 1 except for these points.

(Measurement of Pore Size)

For each cylindrical (tablet-shaped) sample having a diameter of 8.5 mm and a thickness of 1.5 mm obtained in Examples 1 to 3 and Comparative Examples 1 and 2, the pore size was measured in the following manner.

As a pretreatment, samples were dried at a constant temperature of 120° C. for 4 hours. For each sample after the pretreatment, micropore distribution of micropores having a size of 0.0018 μm to 100 μm was determined under the following conditions by the mercury intrusion method using the following measurement device. The obtained micropore distribution curve is shown in FIG. 1.

Measurement device: AutoPore IV9520 (available from Micromeritics Japan)
Measuring Conditions:
  Contact angle between sample and Mercury: 140 deg
  Surface tension of mercury: 0.48 N/m (converted by 1 dyne=$10^{-5}$
The micropore size was calculated by using the following Washburn's equation.

$PD = -4\sigma \cos\theta$  Washburn's equation:

P: Pressure (Pa)
σ: Surface tension of mercury (N/m)
D: Micropore diameter (m)
θ: Contact angle between mercury and sample (deg)

The pore size in the present invention refers to a value of micropore size showing the maximum value of the peak having the largest area in the micropore distribution curve obtained from the measuring pressure by the mercury intrusion method. However, since the micropore size of the pore size distribution curve (Log Differential Intrusion) shown in FIG. 1 is the radius, the pore size of the sample in Example 1 is 7.5×2=15 μm.

(Rate of Pores)

The rate of pores was calculated by using the following formula using the cumulative micropore volume and the total micropore volume measured by the mercury porosimeter.

Rate of pores (%)=(cumulative micropore volume/total micropore volume)×100

For example, in the case of Example 1, the cumulative micropore volume of the range exceeding 71 μm was 0.203 m/g, and the total micropore volume was 6.22 mL/g. Therefore, the rate of pores exceeding 71 μm was 0.203/6.22× 100=3.2%.

Figure 3:
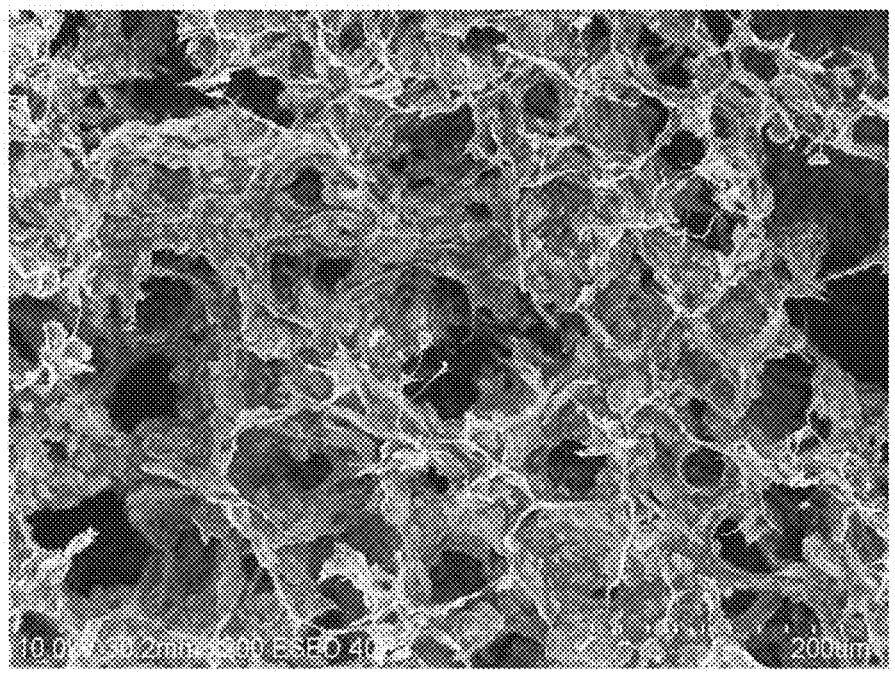
FIG. 3 is an enlarged SEM image of a section of a porous composite prepared in Example 1.
Figure 4:
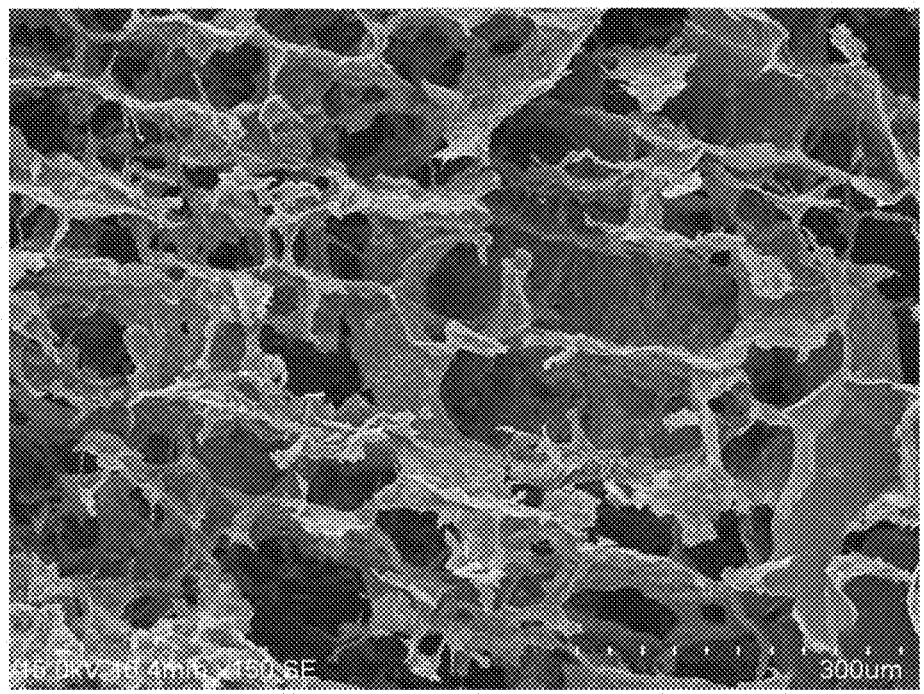
FIG. 4 is an enlarged SEM image of a section of a porous composite prepared in Comparative Example 1.
Figure 5:
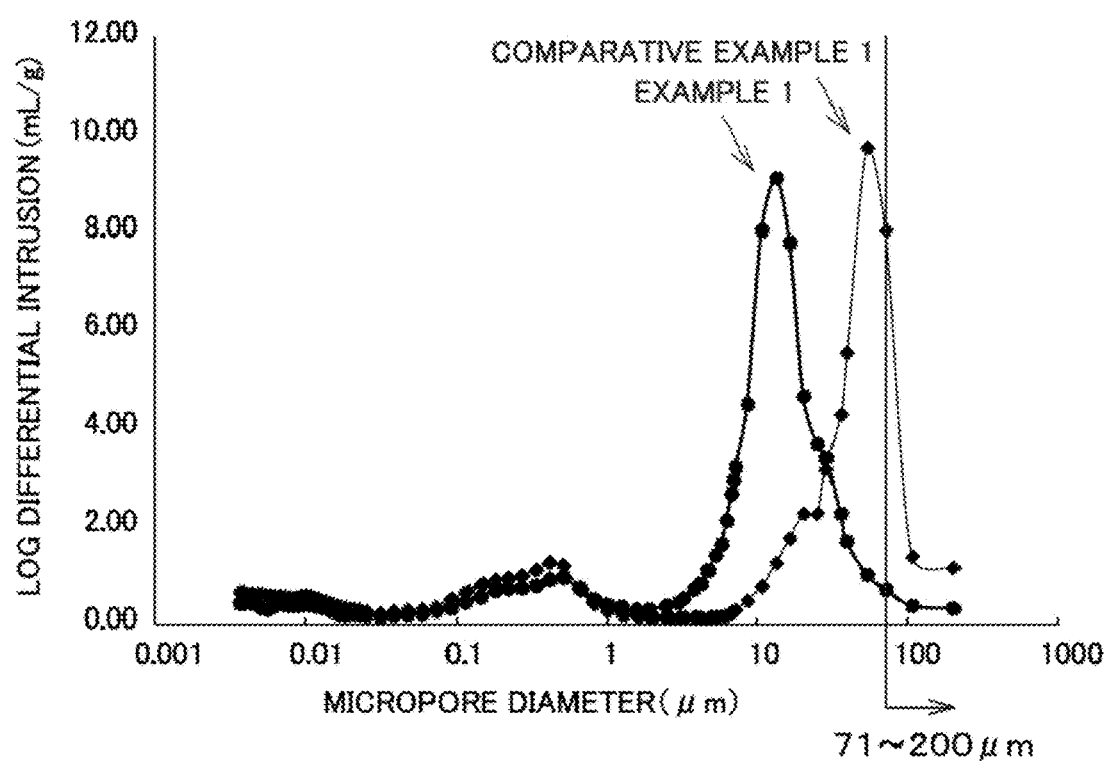
FIG. 5 is a graph for comparison of micropore distribution curves in measurement of pore size between Example 1 and Comparative Example 1.

Further, for three samples prepared in the same condition, measurement of pore size was conducted, and the mean value of the pore sizes was determined. Additionally, the rate of pores in the range of 71 μm to 200 μm in the entire pore size (micropore diameter) distribution curve was determined. The results of measurement of pore size for the examples and comparative examples are shown in Table 1. Further, the appearance of the pore size of Example 1, and the appearance of the pore size of Comparative Example 1 are representatively shown in FIGS. 3 and 4, respectively, and comparison of pore size distribution curves between Example 1 and Comparative Example 1 is shown in FIG. 5.

(Measurement of Compressive Strength)

In an environment at a temperature of 25° C. and a humidity of 65%, a cylindrical specimen (sample) having a diameter of 9.0 mm and a height of 15 mm was dipped in a phosphate buffered saline (10 mM sodium phosphate, 0.14 M sodium chloride, pH 7.4) for 30 minutes. Then, the water on the surface of the sample was lightly wiped, and a uniaxial load was applied as shown in FIG. 2 by using a precision universal tester (Autograph AGS-J, available from Shimadzu Corporation, load cell capacity: 1 kN). The load was varied stepwise, and the least load at which the sample collapsed was determined as a load at collapse.

To be more specific, referring to FIG. 2, after setting sample 1 on sample stage 21, crosshead (pressing jig) 22 is lowered at a speed of 10 mm/min, and when the load cell indicates 2.5 N, crosshead 22 is stopped to release the sample from the load. The sample on the sample stage is observed, and if it is not collapsed, the sample is returned to the sample stage and set again, and the crosshead is lowered similarly until the load cell indicates 5 N. This operation was repeated while the load was increased by 2.5 N every time, and the load when collapse of the sample was first observed was determined as a load at collapse. In this test, the wording "collapse of the sample was observed" means that occurrence of a clear crack or peeling was confirmed when the sample was visually observed.

Compressive strength in the present invention is represented by formula 1, from the load at collapse, and the sectional area of the sample (sectional area in the section perpendicular to the thickness direction of the cylinder).

$Cs = F/S$ (Formula 1)

Cs: Compressive strength WO
F: Load at collapse (N)
S: Sectional area of sample ($m^2$)

The sectional area of the sample was about $(0.0045)^2 \times 3.14 = 6.36 \times 10^{-5}$ $m^2$.

For three samples prepared under the same condition, compressive strength was measured, and the mean value of the compressive strengths was determined. Results of measurement of compressive strength for the examples and comparative examples are shown in Table 1.

TABLE 1

| | Freezing method | Pore size (μm) | Rate of pores of 71 μm to 200 μm (%) | Load at collapse (N) | | | | Compressive strength (MPa) | | | |
|---|---|---|---|---|---|---|---|---|---|---|---|
| | | | | 1 | 2 | 3 | Mean | 1 | 2 | 3 | Mean |
| Example 1 | −80° C. MeOH | 15 | 3.2 | 30.0 | 30.0 | 30.0 | 30.0 | 0.53 | 0.53 | 0.53 | 0.53 |
| Example 2 | −196° C. liquid nitrogen | 7.4 | 4.5 | 27.5 | 25.0 | 27.5 | 26.7 | 0.49 | 0.44 | 0.49 | 0.47 |
| Example 3 | −40° C. MeOH | 36 | 7.6 | 17.5 | 17.5 | 20.0 | 18.3 | 0.31 | 0.31 | 0.35 | 0.32 |
| Comparative Example 1 | −80° C. freezer | 48 | 14.3 | 15.0 | 15.0 | 12.5 | 14.2 | 0.26 | 0.26 | 0.22 | 0.25 |
| Comparative Example 2 | −20° C. freezer | 74 | 42.2 | 10.0 | 7.5 | 7.5 | 8.3 | 0.18 | 0.13 | 0.13 | 0.15 |

Results shown in Table 1 reveal that samples (porous composites) of Examples 1 to 3 that are prepared by dipping in a liquid refrigerant, which is a rapider freezing method than that in the comparative examples, have pore sizes within the range of 5 μm to 40 μm, and have smaller pore sizes than in the comparative examples. It is also revealed that the samples of Examples 1 to 3 having pore sizes within the range of 5 μm to 40 μm have a high compressive strength of greater than or equal to 0.3 MPa.

Regarding the rate of pores of greater than or equal to 71 μm, the samples of Examples 1 to 3 had a rate of less than or equal to 8%, and the samples of the comparative examples had a high rate of greater than or equal to 14%. This reveals that the samples of Example 1 to 3 have a narrow distribution of pore size, and thus have more uniform structural characteristics. Porosity of Example 1 was 89%, and porosity of Comparative Example 1 was 92%.

It is to be understood that any embodiments and examples disclosed herein are illustrative but are not restrictive in every point. The scope of the present invention is specified by claims rather than by the aforementioned description, and is intended to involve all modifications within the meaning and scope equivalent to the claims.

INDUSTRIAL APPLICABILITY

Since the porous composite, and the bone regeneration material containing the same of the present invention have excellent operability owing to both the easy workability and the mechanical strength, and high bone regenerative capability, it is useful for repair of bone defects mainly in the dental/oral surgery field, or the orthopedic surgery field.

The invention claimed is:

1. A porous composite, comprising:
octacalcium phosphate and collagen,
wherein the octacalcium phosphate is present as granules in the porous composite,
wherein the porous composite comprises pores having a size of 5 μm to 40 μm,
wherein the pore size is a value of micropore diameter showing a maximum value of a peak having a largest area in a micropore distribution curve obtained by measuring pressure by a mercury intrusion method using a mercury porosimeter,
wherein a volume of pores having a size of 71 μm to 200 μm divided by a volume of all pores having a size of less than or equal to 200 μm, multiplied by 100, is less than or equal to 8% and more than 0%, and
wherein said porous composite has a compressive strength of greater than or equal to 0.3 MPa.

2. A bone regeneration material comprising the porous composite according to claim 1.

3. A method for producing a porous composite comprising octacalcium phosphate and collagen, comprising the steps of:
(a) adding particles of octacalcium phosphate to a collagen solution,
(b) freezing a gel, sol or liquid containing octacalcium phosphate and collagen, and
(c) lyophilizing the frozen gel, sol or liquid,
wherein said porous composite has a compressive strength of greater than or equal to 0.3 MPa, and
wherein the freezing of step (b) is performed by dipping the gel, sol or liquid containing octacalcium phosphate and collagen in a liquid refrigerant.

4. The porous composite according to claim 1, wherein porosity of the porous composite is 80% to 98%.

5. The porous composite according to claim 4, wherein the granules include granules having a diameter of 10 μm to 1000 μm.

6. The porous composite according to claim 5, wherein the collagen forms a spongy structure.

7. The porous composite according to claim 5, wherein the granules include granules having a diameter of 300 μm to 500 μm.

8. The porous composite according to claim 7, wherein the collagen forms a spongy structure.

9. The porous composite according to claim 7, wherein ratio of octacalcium phosphate in the porous composite to 1 part by weight of collagen in the porous composite is 0.5 parts by weight to 35 parts by weight.

10. The porous composite according to claim 9, wherein the collagen forms a spongy structure.

11. The method for producing a porous composite according to claim 3, wherein the temperature of the liquid refrigerant is less than or equal to −20° C.

12. The method for producing a porous composite according to claim 11, wherein the liquid refrigerant is at least one selected from the group consisting of methanol, ethanol, acetone, acetonitrile, and liquid nitrogen.

13. The method for producing a porous composite according to claim 12, wherein the temperature of the liquid refrigerant is less than or equal to −40° C.

14. The method for producing a porous composite according to claim 3, further comprising, after steps (a)-(c), the step of:

(d) subjecting the lyophilized product obtained by the step (c) to a heat treatment at 50° C. to 200° C.

15. The method for producing a porous composite according to claim 11, further comprising, after steps (a)-(c), the step of:
   (d) subjecting the lyophilized product obtained by the step (c) to a heat treatment at 50° C. to 200° C.

16. The method for producing a porous composite according to claim 12, further comprising, after steps (a)-(c), the step of:
   (d) subjecting the lyophilized product obtained by the step (c) to a heat treatment at 50° C. to 200° C.

17. The method for producing a porous composite according to claim 13, further comprising, after steps (a)-(c), the step of:
   (d) subjecting the lyophilized product obtained by the step (c) to a heat treatment at 50° C. to 200° C.

* * * * *